United States Patent [19]

Fang et al.

[11] 3,996,007

[45] Dec. 7, 1976

[54] TIME-TEMPERATURE INTEGRATING INDICATOR

[75] Inventors: Shou-Mean Fang, Lake Hiawatha; Craig R. Hof, Hopatcong, both of N.J.

[73] Assignee: Bio-Medical Sciences, Inc., Fairfield, N.J.

[22] Filed: Oct. 29, 1975

[21] Appl. No.: 626,981

Related U.S. Application Data

[63] Continuation-in-part of Ser. No. 515,165, Oct. 16, 1974, Pat. No. 3,932,134.

[52] U.S. Cl. .................. 23/253 TP; 116/114 AM; 426/88
[51] Int. Cl.² ............... G01N 21/06; G01N 21/20; G01N 31/22
[58] Field of Search ........ 23/253 TP; 116/114 AM; 426/87, 88

[56] References Cited

UNITED STATES PATENTS

| | | | |
|---|---|---|---|
| 3,420,205 | 1/1969 | Morison | 116/114 |
| 3,695,903 | 10/1972 | Telkes et al. | 99/192 T |
| 3,768,976 | 10/1973 | Hu et al. | 23/253 TP |
| 3,888,631 | 6/1975 | Stürzinger | 23/253 TP |

*Primary Examiner*—Robert M. Reese
*Attorney, Agent, or Firm*—Anthony Langani, Jr.

[57] ABSTRACT

A pouch for containing the gas generating means in a Time-Temperature Indicator which comprises a rate controlling film formed into a sealed pouch having contained therein a frangible ampule containing the gas generating means, said ampule being enclosed in a porous medium, said medium containing an indicator composition responsive to the gas generated by the gas generating means, so as to indicate a color change thereby making the user aware that the gas ampule has been broken.

7 Claims, 6 Drawing Figures

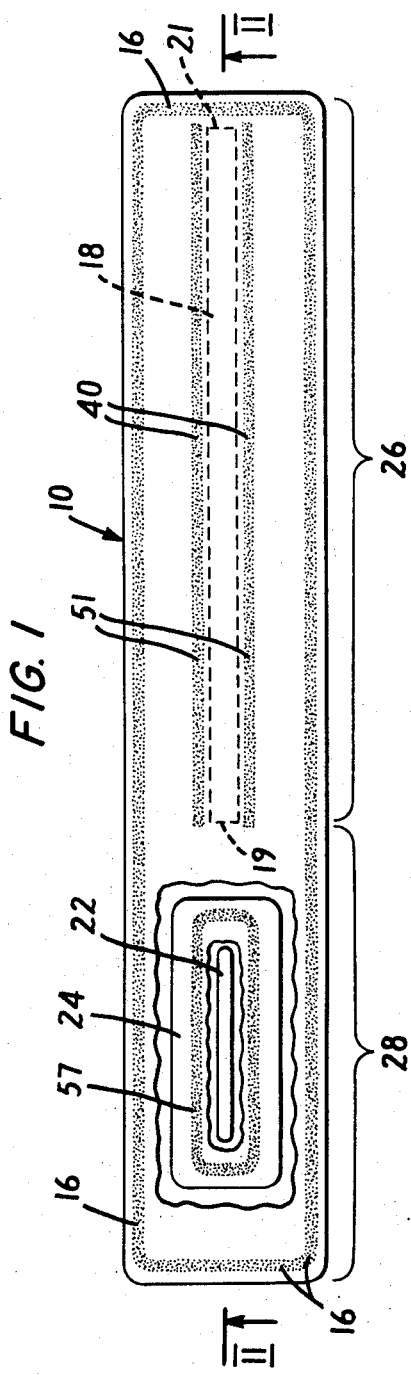
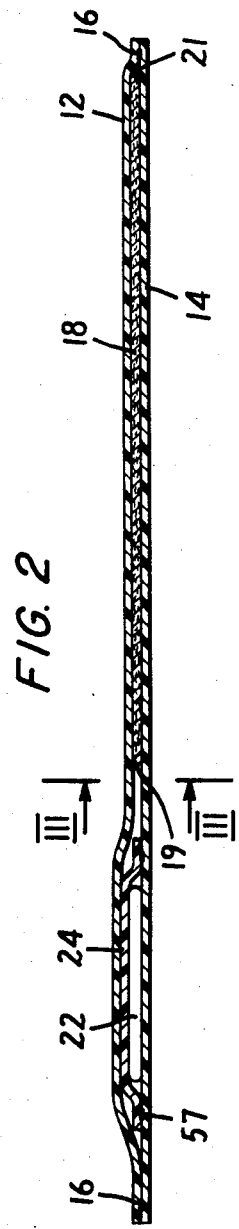
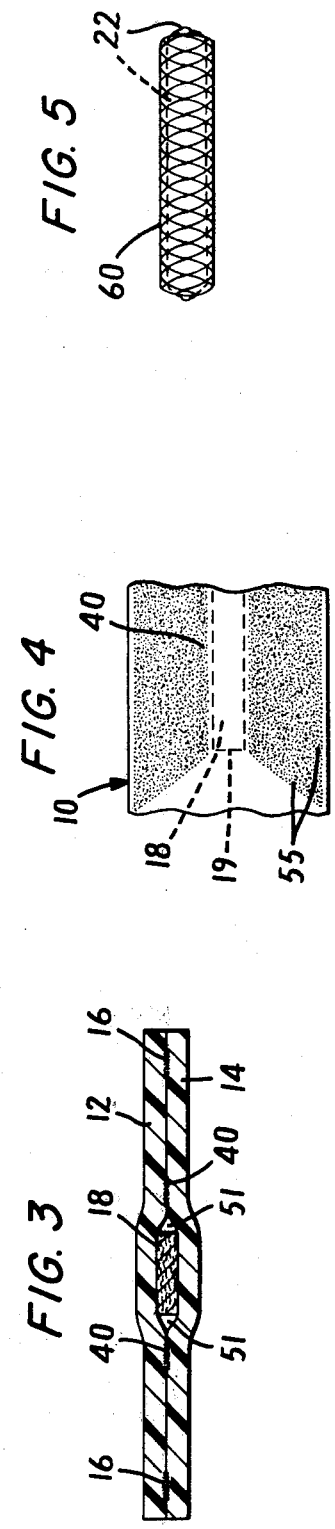

TIME-TEMPERATURE INTERGRATING INDICATOR

CROSS REFERENCE TO RELATED APPLICATIONS

This application is a continuation-in-part of U.S. Pat. application Ser. No. 515,165, filed Oct. 16, 1974 now U.S. Pat. No. 3,932,134.

BACKGROUND OF THE INVENTION

Time-Temperature Integrating Indicators have been disclosed in co-pending U.S. application Ser. No. 469,851, filed on May 14, 1974 of Larsson, now a U.S. Pat. No. 3,946,611. The device disclosed in that application incorporated herein by reference, includes an elongated envelope of upper and lower walls of gas impervious material which are heat sealed together in a continuous course extending around the periphery of each, with the walls further having a traverse cross seal intermediate the ends of the envelope so as to define a first and second compartment in the envelope. A gas generating material is disposed in the first compartment and a wick means extends from the first compartment to the second compartment and through the cross seal, whereby the wick means is the only gas communication between the first and second compartment. Further, an indicator composition is deposited on the wick with the indicator composition producing a color change in the presence of a gas generated by the gas generating material. The function of the device is to provide a temperature history, e.g. of a product associated with the device in the visual display as a color front of the indicator wick with the distance of the front advancement being a function of the temperature-time interval, the visual display serving to inform a user whether or not the product has been unduly subjected to adverse temperature conditions as might affect the ultimate product usage. The device is particularly suited for providing an indication of conditions of foods, films, pharmaceuticals, biological preparations and similar products to give indication of decomposition, deterioration or changes of the such composition or products.

Our co-pending application, Ser. No. 515,165, filed on Oct. 16, 1974 describes an improved method of forming the seal about the periphery of the device in such a manner as to eliminate the need for the cross seal. The purpose of the cross seal is to prevent spurious random gas molecule transport within the Time-Temperature Integrating Indicator Device, which if not prevented, would give erroneous readings. Our U.S. application Ser. No. 515,165 now U.S. Pat. No. 3,932,134 incorporated herein by reference teaches a structure which eliminates such spurious random gas molecule transport as a factor in the operation of the device by providing a longitudinally disposed gas barrier means extending between the indicator envelopes upper and lower walls immediate the adjacent longitudinal margin of the wick and along substantially the full length of the wick. If any gas should bypass the ends of the wick nearest the gas source, the spaces between the barrier and wick's side margin is sufficiently small to insure that the gas will not travel longitudinally of the wick to any appreciable or significant distance before it is caused to come into contact with the wick. Thus substantially all the gas absorbed by the wick is caused to make first contact with the wick at or right adjacent to the end of the wick closest to the gas source.

Both of the prior art devices require the use of a rate controlling film in order to control the rate of flow of the gas generating means from the first compartment, which encloses the gas generating means and the second compartment in which is contained the wicking means. The rate at which gas permeates through the rate controlling film is temperature dependent and will determine the response of the device to changes in temperature and time. This rate controlling film as described in the prior art devices is sealed either thermally or adhesively between the upper and lower walls of the device. Such construction causes difficulties in manufacture and assembly of the device.

SUMMARY OF THE INVENTION

It surprisingly has been found that an improved Time-Temperature Integrating Indicator device may be prepared using a sealed pouch, at least a part of which is made of rate controlling film to enclose the gas generating means. The gas generating means is incorporated in an ampule or other suitable frangible enclosure and surrounded by a porous material, which has been impregnated with an indicator composition which is responsive to the gas generated to produce a color change.

BRIEF DESCRIPTION OF DRAWINGS

FIGS. 1–5: Structural Configuration of Time-Temperature Indicator.

DETAILED DESCRIPTION

Figure 6:
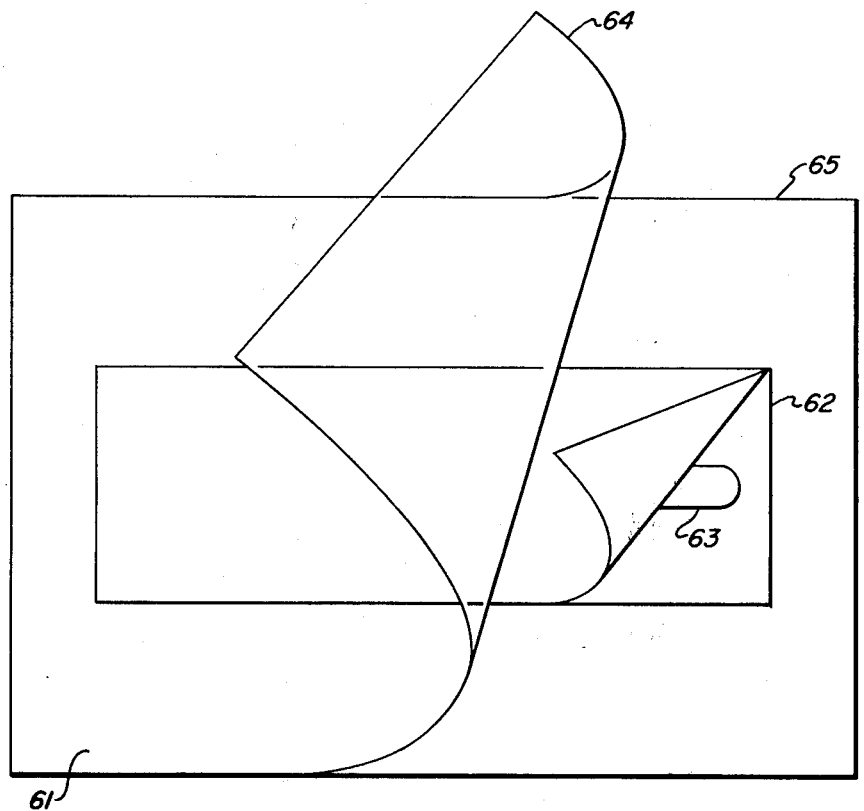
FIG. 6: Structural Configuration of pouch containing gas generating means.

This invention relates to an improved method of containing a gas generating means in a Time-Temperature Integrating Indicator as well as an improved method for incorporating a rate controlling the film in the Indicator. As used in the specifications and claims, the term of the Time-Temperature Integrating Indicator means the devices disclosed in U.S. application Ser. No. 469,851, filed May 14, 1974 now a U.S. Pat. No. 3,946,611 U.S. application Ser. No. 515,165 filed Oct. 16, 1974, now U.S. Pat. No. 3,932,134 and U.S. Application Ser. No. 615,300, filed on or about Sept. 22, 1974, in the name of Raymond P. Larsson, all of which applications are incorporated herein by reference. For the purpose of brevity, the device will be referred to hereinafter as Time-Temperature Indicator or TTI.

The TTIs taught in the prior art operate on the principle that certain dyes are sensitive to changes in pH and that certain chemical compounds display a color change when complexed with other compounds. A gas generating means generates a gas which then permeates through a rate controlling film which rate controlling film has a permeability with respect to such gas which is temperature dependent. The gas which has permeated through the rate controlling film (RCF) is absorbed into a wick means which has incorporated therein an indicator composition which may include humectants and quantifiers as well as a substance which is responsive to the gas and displays a color change when contacted by such gas.

As used in the specifications and claims the term "indicator compositions" means a pH sensitive dye or a chemical compound which will react or complex with the gas generated to display a color change. The terms also includes the dye or compound when associated with humectants and quantifiers. Application Docket Number BMS 47 of Larsson incorporated herein by reference teaches various humectants and quantifiers which may be incorporated into the indicator composition.

Illustrative non-limiting examples of pH sensitive dyes useful as indicator compositions in the practice of this invention are phenolphthalein, xylenol blue, nile blue A, m-cresol purple, bromocresol green, O-cresol red, cyanidine chloride, bromocresol purple, alizarin, thymol blue, bromophenol red, methyl red, acid fuchsin, brilliant yellow, logwood extract, bromothymol blue, phenol red, etc. Various compounds such as copper or cobalt halides which can form complexes (e.g. with ammonia or $H_2O$) which exhibit a color change upon complexing may be used as in the indicator composition instead of the pH sensitive dye.

An additional compound preferably included in the wick is a quantifier material whose function is to fix the time interval over which the Time-Temperature Indicator is operative.

The temperature sensitivity and hence, the $Q_{10}$ of the Time-Temperature Indicator is determined by the temperature coefficients of both the vapor pressure of the gas generated and the permeability of the rate controlling film (RCF); the time response of the indicator, on the other hand, is determined by the amount of quantifier impregnated on the wick, as well as the nature, thickness, and effective area of the RCF.

Variations in the quantity of quantifier are best accomplished by controlling its concentration in an impregnating solution. For example, where the quantifier material is tartaric acid, a solution is prepared of 0.2N tartaric acid in ethanol and glycerol, the glycerol comprising 20% of the volume of the solution, and 0.2% of phenol red based on the total solution. The wick is immersed in the solution and the excess material squeezed out by passing the saturated wick through a roll nip and allowing the wick to air dry.

Where the RCF is polypropylene of an area of about 525mm² and the gas generating material is $(NH_4)_2CO_3$, the indicator based on a wick prepared in the above matter has a time scale at 0° F of about 600 days for ¼ × 4-inch wick of 6 mil Whatman No. 114 filter paper. This time scale may be shortened by reducing the concentration of quantifier material in the impregnating solution.

The requirements of the quantifier are that it (1) have a low
volatility e.g. no substantial loss over the life of the device and (2) react rapidly and stoichiometrically with the gas generated to form a stable compound.

By reacting rapidly it is meant that the reaction rate of the quantifier with the gas is sufficiently rapid so that it consumes the gas generated at least as quickly as the gas permeates through the rate controlling film.

The quantifier itself must be stable and not decompose in the presence of the other constituents of the indicator composition. Hence, the quantifier materials of choice are acid or basic compounds which can be dissolved for deposition on the wick. The indicator composition can also include a germicide or bacteriocide as well as the pH indicator and quantifier. It is also desirable to include a humectant in the indicator composition. Preferably the humectant is normally liquid at the use temperature of the device.

Where the gas generated is a basic gas, quantifiers useful in the practice of this invention have dissociation constants ($pK_a$) of about 7 or less; preferably about 6 or less illustrative examples of quantifiers useful with basic gases are organic acids such as trichloroacetic acid, maleic acid, malonic acid, succinic acid, lactic acid, cinnamic acid, oxalic acid, glycolic acid, malic acid, tartaric acid, etc., and potassium phosphate (mono basic).

Where the gas generated is an acid, e.g. $C_1$–$C_6$ organic acid, the quantifiers useful in the practice of this invention have basic dissociation constants ($pK_b$) of about at least 7, preferably about at least 8. Illustrative examples of such quantifiers are alkali metal compounds such as NaOH, $Na_2CO_3$, $Na_2(HPO_4)$ $Li_2CO_3$; quaternary ammonium hydroxides such as tetramethyl ammonium hydroxide, benzyl trimethyl ammonium hydroxide etc.; and amines such as imidazole, Tris (hydroxymethyl) aminomethane, quinine, guanidine, etc.

With continuing reference to FIGS. 1–3, there is depicted the prior art TTI as shown in our co-pending U.S. application Ser. No. 515,165 comprising an envelope, 10, comprised of elongated, generally co-extensive upper and lower walls, 12, and, 14, of gas impermeable material.

The walls, 12, and, 14, while depicted as single ply components of transparent material could be multi-ply and be laminated to include a metal foil layer as well as being in part opaque. The important consideration is that said walls be gas impermeable. Walls, 12, and, 14, are joined together to form the envelope structure by sealing them together in a continuous course extending about the periphery of each, e.g., by heat-sealing, the material of the walls of course being compatible to that purpose, and such peripheral seal being shown generally at, 16, in FIG. 2. The device also embodies a wick, 18, the wick being disposed longitudinally of the envelope, 10, in a longitudinal portion thereof which constitutes an indicating section, 26, and being treated with an indicator composition.

The device also includes an ampule, 22, disposed in another longitudinal portion of the envelope constituting a gas generation section, 28, in which is confined a gas generating material, the ampule being disposed intermediate the upper and lower walls, 12, and, 14, and being fixedly positioned there-between as by connection of an overlaying gas permeable sheet, 24, with one of said walls, the wick, 18, having one tip as at, 19, in gas generation section 26 and its other tip end, 21, remote from said gas generation section.

There is further provided a gas barrier, 40, at each longitudinal side of the wick, 18, the gas barrier extending between walls, 12, and, 14, and in the instance where walls, 12, and 14, are amenable to heat sealing being provided by effecting a heat sealed joinder of the walls in the pattern depicted best in FIG. 1. The heat seal is positioned immediately adjacent the said wick longitudinal side margins. "Immediately adjacent" as used herein is intended to mean affecting the heat seal as close to the wick as practical manufacturing will permit without causing adherence of any melted wall material to the wick material. Thus, any spacing, 51, as may exist between the sides of the wick at the barrier is of insignificant consequence with respect to the possibility of gas transport occurring along said space without making a contact with the wick, 18, at or very close to tip end, 19. In this manner the possibility of random gas molecules transport through said space and into first contact with the wick at location remote from tip end, 19, is inhibited.

The important requirement in the construction of the device is that the longitudinal gas barrier extends immediately adjacent the wick side margins substantially along the full length of the wick. If desired, however, the sealed joinder of the envelope walls can be extended laterally outwardly from the wick sides in the pattern, 55, depicted in FIG. 4.

Further, the gas generating component is confined within ampule, 22, and the ampule, 22, is fixedly secured to the inner surface of one of the envelope upper and lower walls, in the depicted embodiment the ampule, 22, being fixedly positioned by securing the same to the inner surface of lower wall, 14, with the gas permeable sheet, 24, the latter being heat sealed to the lower wall in the generally oval course seal pattern, 57, depicted in FIG. 1. The ampule 22, in which the gas generating material is confined desirably is an elongated component, closed at its ends and made of a frangible material, glass being preferred. Thus, when it is desired to activate the device, the user need only apply a bending force to the envelope in the region of the position of the ampule and generally applied the intermediate the ends of the ampule to fracture the same and permit the gas to escape in the first section, 26, of the envelope from whence it can flow onto the wick located in the second section, 28. To provide that when ampule, 22, is ruptured, resulting jagged particles of the same will not pierce or damage any of the envelope structure, the ampule can be enclosed in a resilient sleeve, 60, as shown in FIG. 5, the resilient sleeve for example being a braided fiberglass member. It will be obvious to those skilled in the art that the gas generating material need not necessarily be sealed in an ampule.

Illustrative examples of humectants useful in the practice of this invention are polyols such as ethylene glycol, propylene glycol, glycerol, mannitol etc.; salts such as sodium iodide, sodium bromide, sodium nitrate, etc.

An alternative to the longitudinal seals described above is a seal transverse and perpendicular to the wick, 18, at or near the end of the wick, 19, near the gas generating section 28. This transverse seal divides the device into its two sections, 26, and 28. The function of the transverse seals or the heretofore described longitudinal seals is to prevent access to the wick, 18, of the gas generated except by capillary wicking action along the wick, 18, beginning at the end, 19, which protrudes into the gas generating section, 28. Absent these seals, gas would be free to diffuse toward the far end of the wick, 21, thereby giving erroneous readings. The transverse seal is described in detail in U.S. application Ser. No. 469,851 now U.S. Pat. No. 3,946,611.

The gas generation section, 26, can utilize a variety of physical or chemical processes. In its simplest embodiment, the gas generation may involve simple sublimation or vaporization and thus one may utilize any substance which has a vapor pressure, as, for example, water (or ice); iodine; alcohols; hydrogen peroxide; lower alkanoic and aromatic acids, such as acetic acid; acid anhydrides such as maleic anhydride; acid halides, etc. Alternatively the gas generating material can be a salt which decomposes with the generation of a gas, as for example ammonium carbonate, sodium bicarbonate, ammonium acetate, ammonium oxalate, ammonium formate and the like. In those instances in which the rate of gas generation corresponds to the rates being monitored, it is unnecessary to include the barrier film, and gas generating section of the envelope, 28, can have a single chamber. Even in such embodiments, however, it is often desirable to interpose a highly permeable physical barrier which separates the gas generating material from the wick.

In its preferred embodiment a rate controlling film (RCF) is interposed between the gas generating means and the wick means. Typical of these temperatures dependent rate controlling films (RCF) are polyethylene, polypropylene, nylon, esters of polyethylene glycol and terephthalic acid (mylar), cellulose films and the like. It can be shown mathematically that the contribution of the gas generation and the contribution of gas transport to the $Q_{10}$ of the system are cumulative so that by judicious selections of the two systems it is possible to achieve an overall effect in which the change in rate of gas availability at the wick with changes in temperature parallel the $Q_{10}$ of the product being monitored.

The improvement of this invention comprises substituting for gas permeable sheet, 24, a pouch of gas permeable film to act as the RCF for the TTI. Referring now to FIG. 6 the pouch, 61, encloses an ampule, 62, which contains the gas generating means. This ampule, 62, is itself enclosed in a protective layer, 63, which serves to both protect the RCF pouch, 61, from damage by fragments of the ampule, 62, and to contain such fragments.

In a preferred embodiment the protective layer, 62, is impregnated with a pH sensitive dye or with the indicator composition containing the pH sensitive dye or complexing compound. Where thus impregnated the protective layer, 62, serves to indicate by a color change that the ampule containing the gas generating means is broken either upon activation or inadvertently. Additionally, the impregnated protective layer serves as a quality control indicator since leaky ampules will result in a color change in the impregnated protective layer. Hence, such leakers can be discarded in advance of the final fabrication of the TTI.

As used in the specification and claims the term "ampule" is intended to mean any suitable container for the gas generating means which is readily frangible or otherwise rupturable. In its preferred embodiment the ampule is a sealed glass vial.

The protective layer may be a glass sheath such as the resilient sheath, 60, of FIG. 5 or it may be a separate pouch in the form shown in FIG. 6. Its composition may be woven glass fiber, woven natural or synthetic fiber, e.g. Dacron; non-woven fiber, e.g. non-woven polyethylene, etc. The protective layer must not be a barrier for the gas; that is, it must have a structure which permits the free passage of gas therethrough. Hence, it should comprise woven or non-woven fabric and should not be a continuous film. In the alternative a normally impervious material, e.g. natural or synthetic rubber may be used provided that it is perforated.

Illustrative non-limiting examples of suitable materials for the protective layer are spun bonded polyethylene, a non-woven fabric sold under the duPont trademark Tyvek; non-woven polyester fabric e.g. non-woven Dacron (duPont's brand of polyethylene terephthalate ester); a porous composition sold under the trademark Acropor which is a microporous acrylic-polyvinyl chloride copolymer deposited on a non-woven nylon cloth; non-woven polypropylene; non-woven nylon; etc.

The preferred materials for the protective layer are those materials which can be heat sealed and impregnated with indicator composition. In a preferred embodiment a glass ampule containing the gas generating means is deposited on a sheet of Tyvek which has been embossed to form a pocket to contain the ampule. A second sheet of Tyvek is placed over the first sheet and the two sheets are heat sealed together.

In one embodiment of the invention, both the upper surface, 64, and the lower surface, 65, of the pouch, 61, are made of RCF material. In another, embodiment one surface e.g. the lower surface, 65, may be a gas impervious layer such as polyvinylidene chloride or polyethylene coated aluminum.

The term "heat sealed" is intended to include any method of the seal which depends on the melt and fusion of the material e.g. impulse sealing, ultrasonic welding, etc.

Although the pouch is referred to as being made of RCF or having at least one surface of such material it will be obvious to those skilled in the art that only a minor portion of the pouch need be RCF. For example, the pouch may be made entirely of a polyethylene/aluminum laminate with a small window of RCF. The RCF may be heat sealed to the polyethylene and the pouch formed by sealing the polyethylene surfaces of the laminate to each other. The area of the window would depend on the operating parameters of the device. Of course, the aluminum serves only as a gas impervious layer and any gas impervious equivalent may be substituted therefor. As used in the specification and claims the term "gas impervious" means a material which is preferably at least an order of magnitude less permeable to the gas generated than the RCF.

The term "protective layer" as used in the specification and claims means the afore-described protective layers which are characterized by being highly permeable to the gas. Preferably the "protective layer" is of composition which may be impregnated with indicator composition. The term "highly permeable" means having a permeability such that the rate of gas diffusion through the protective layer is at least five times more rapid than through the RCF; preferably at least 10 times as fast.

What is claimed is:

1. In a Time-Temperature Indicator comprising a gas generating means, a rate controlling film and a wicking means having incorporated therein an indicator composition the improvement which comprises the gas generating means being contained in an ampule surrounded by a protective layer and enclosed in a sealed pouch at least a part of which pouch is made of rate controlling film material.

2. The Indicator of claim 1 wherein the protective layer is non-woven polyethylene fabric.

3. The indicator of claim 1 wherein the ampule is a sealed glass vial.

4. The Indicator of claim 1 wherein the pouch comprises an upper surface and a lower surface wherein one of said surfaces comprises a rate controlling film and the other surface is a gas impervious material.

5. The Indicator of claim 1 wherein the gas generating means is acetic acid or ammonium carbonate.

6. The Indicator of claim 1 wherein the protective layer is impregnated with indicator composition.

7. The Indicator of claim 6 wherein the indicator composition includes a pH sensitive dye.

* * * * *